US008281445B2

(12) United States Patent
Adkins, Jr. et al.

(10) Patent No.: US 8,281,445 B2
(45) Date of Patent: *Oct. 9, 2012

(54) HEATED EYELID CLEANSER

(75) Inventors: Nat G. Adkins, Jr., Richmond, TX (US);
Daniel Banov, Sugar Land, TX (US);
August Bassani, Houston, TX (US);
Patrick Witham, Eugene, OR (US)

(73) Assignee: OCuSOFT, Inc., Rosenberg, TX (US)

( * ) Notice: Subject to any disclaimer, the term of this patent is extended or adjusted under 35 U.S.C. 154(b) by 528 days.

This patent is subject to a terminal disclaimer.

(21) Appl. No.: 12/486,970

(22) Filed: Jun. 18, 2009

(65) Prior Publication Data

US 2009/0300864 A1    Dec. 10, 2009

Related U.S. Application Data

(63) Continuation-in-part of application No. 11/592,684, filed on Nov. 3, 2006, now Pat. No. 7,951,387.

(60) Provisional application No. 61/132,593, filed on Jun. 20, 2008.

(51) Int. Cl.
*B08B 1/00* (2006.01)
*A61F 7/00* (2006.01)

(52) U.S. Cl. ............... 15/104.93; 607/109; 607/114

(58) Field of Classification Search ............... 15/104.93; 604/294, 289–291; 607/109, 114
See application file for complete search history.

(56) References Cited

U.S. PATENT DOCUMENTS

| | | | |
|---|---|---|---|
| 2,573,791 A | 4/1947 | Howells |
| 3,068,863 A | 12/1962 | Bowman |
| 3,092,103 A | 6/1963 | Mower |
| 1,167,249 A | 10/1969 | Ambler et al. |
| 3,908,645 A | 9/1975 | Sandvig |
| 4,654,208 A | 3/1987 | Stockel et al. |
| 4,682,371 A | 7/1987 | Heltman |
| 4,758,595 A | 7/1988 | Ogunbiyi et al. |
| 4,904,698 A | 2/1990 | Adkins, Jr. et al. |
| 5,246,695 A | 9/1993 | Hintz et al. |
| 5,431,622 A | 7/1995 | Pyrozyk et al. |
| 5,470,875 A | 11/1995 | Merianos et al. |
| 5,662,624 A | 9/1997 | Sundstrom et al. |
| 5,702,992 A | 12/1997 | Martin et al. |
| 5,769,806 A | 6/1998 | Radow |
| 5,879,378 A | 3/1999 | Usui |
| 5,942,218 A | 8/1999 | Kirschner et al. |
| 6,045,817 A | 4/2000 | Ananthapadmanabhan et al. |
| 6,090,060 A | 7/2000 | Radow |
| 6,112,900 A | 9/2000 | Adkins, Jr. |
| 6,207,628 B1 | 3/2001 | Soyer et al. |
| 6,257,759 B1 | 7/2001 | Wintonsky et al. |
| 6,320,094 B1 | 11/2001 | Arnold et al. |
| 6,409,746 B1 | 6/2002 | Igaki et al. |
| 6,604,854 B1 | 8/2003 | Limburg et al. |
| 6,623,517 B1 | 9/2003 | DeLuisa et al. |
| 6,629,964 B1 | 10/2003 | Ono et al. |
| 6,846,846 B2 | 1/2005 | Modek et al. |
| 7,231,922 B2 | 6/2007 | Davison et al. |
| 2001/0036964 A1 | 11/2001 | Clarkson et al. |
| 2002/0128170 A1 | 9/2002 | DeClercq et al. |
| 2004/0259951 A1 | 12/2004 | Clarkson et al. |
| 2005/0022823 A1 | 2/2005 | Davison et al. |
| 2005/0048139 A1 | 3/2005 | Modek et al. |
| 2005/0238602 A1 | 10/2005 | Modek et al. |
| 2005/0261401 A1 | 11/2005 | Wood et al. |
| 2005/0281762 A1 | 12/2005 | Modek et al. |
| 2006/0036220 A1 | 2/2006 | Kawahara et al. |
| 2006/0093634 A1 | 5/2006 | Lutz et al. |
| 2006/0210616 A1 | 9/2006 | Linder |
| 2006/0246013 A1 | 11/2006 | Adkins, Jr. |

FOREIGN PATENT DOCUMENTS

| | | |
|---|---|---|
| WO | WO 02/092049 A2 | 11/2002 |
| WO | WO 02/092049 A3 | 4/2003 |
| WO | WO 03/069994 | 8/2003 |
| WO | WO 2004/064817 A1 | 8/2004 |
| WO | 2005097130 A1 | 10/2005 |
| WO | WO 2005/097130 | 10/2005 |
| WO | WO 2006/045743 | 5/2006 |
| WO | WO 2007/120817 A1 | 10/2007 |

OTHER PUBLICATIONS

Taiwanese Office Action dated Feb. 10, 2012 for co pending Taiwanese patent app. No. 098120683.
Chinese Office Action dated Feb. 22, 2012 for co-pending Chinese patent app. No. 200780041027X.
Examiners Report, AU, Mar. 4, 2010.
Olsen et al. Abstract: "Increase in tear film lipid layer thickness following treatment with warm compresses in patients with meibomian gland dysfunction." Apr. 2003 http://www.ncbi.nlm.nih.gov/entrez/query.fcgi?cmd=Retrieve&db=PubMed&list_uids=12695712&dopt=Abstract.
Greiner J.V. et al.: "Effects of Eyelid Scrubbing on the Lid Margin" The CLAO Journal, vol. 25, No. 2, Apr. 1999, pp. 109-113 http://journals.lww.com/claojournal/Abstract/1999/04000/Effects_of_Eyelid_Scrubbing_on_the_Lid_Margin.10.aspx.

(Continued)

*Primary Examiner* — Michael G Hartley
*Assistant Examiner* — Jagadishwar Samala
(74) *Attorney, Agent, or Firm* — D'Ambrosio & Menon, PLLC

(57) ABSTRACT

Embodiments of the invention include a heated eyelid cleansing apparatus, a method of manufacturing a heated eyelid cleansing apparatus, a kit for providing treatment to the eyelids, and a method for cleansing an eyelid with a heated eyelid cleansing composition. The apparatus comprises an eyelid cleansing composition, a fabric pad impregnated with the eyelid cleansing composition, and a heating element. The heating element may be encased within the fabric pad or it may be external to the fabric pad.

27 Claims, 2 Drawing Sheets

OTHER PUBLICATIONS

Polack F.M. et al., Liebowitz H.M. et al.: "Experience with a new detergent lid scrub in the management of chronic blepharitis" Arch Opthalml, vol. 106, No. 6, Jun. 1988, pp. 719-720. http://archopht.jamanetwork.com/article.aspx?articleid=637270#References.

"Blepharitis" The Eye Digest May 5, 2003,pp. 1-4. www.agingeye.net/otheragingeye/blepharitis.php.

Hannsmann F. et al: Polyhexamethylenbiguianid (PHMB) aur praoperativen Antisepsis bei Kataraktoperation: Der Opthalmologe, vol. 4 Apr. 2004, pp. 377-383 (Polyhexamethlybiguanid as a preoperative antiseptic for cataract surgery). http://www.ncbi.nlm.nih.gov/pubmed/15067419.

Key J.M., "A Comparative Study of Eyelid Cleaning Regimens in Chronic Blepharitis" The CLAO Journal, vol. 22, No. 3, Jul. 1996, pp. 2009-2212, Dept. of Ophthalmology, Baylor College of Medicine, Houston, TX, USA.

"OCuSOFT Lid Scrub" Apr. 26, 2005. http://www.ocusoftlidscrub.com/.

OCuSOFT® Lid Scrubs, http://www.ocusoft.com/about_htm/fr_ab_prod.htm [downloaded Apr. 26, 2005].

Novartis Ophthalmics Eye Scrub®, http://www.novartisophthalmics.ca/e/products/pi/lidcare.pdf [downloaded Apr. 26, 2005].

Aging Eye Times, [Online], May 5, 2003,pp. 1-4, retrieved from www.agingeye.net/otheragingeye/blepharitis.php (retrieved on Apr. 2, 2008).

Hannsmann F. et al: Polyhexamethylenbiguianid (PHMB) aur praoperativen Antisepsis bei Kataraktoperation: Der Opthalmologe, vol. 4 2004, pp. 377-383, XP00247453.

Key J.M.: A Comparative Study of Eyelid Cleaning Regimens in Chronic Blepharitis: The CLAO Journal, vol. 22, No. 3, Jun. 1996, pp. 2009-2120, XP009093078.

Greiner J.V. et al.: "Effects of Eyelids Scrubbing on the Lid Margin" The CLAO Journal, vol. 25, No. 2, Apr. 1999, pp. 109-113, XP009098075.

Polack F.M. et al., Liebowitz H.M. et al.: "Experience with a new detergent lid scrub . . . chronic blepharitis . . ." Arch Opthalml, vol. 106, Jun. 1988, pp. 719-720, XP009098098.

HEATED EYELID CLEANSER

PRIORITY AND CROSS-REFERENCE TO RELATED APPLICATIONS

This application claims priority to and benefit from U.S. Provisional Patent Application Ser. No. 61/132,593 filed Jun. 20, 2008. This application is a continuation in part of U.S. patent application Ser. No. 11/592,684 filed Nov. 3, 2006, incorporated by reference herein in its entirety.

BACKGROUND OF THE INVENTION

The eyelids are important to overall ocular health because they protect the eyes from dangers such as approaching objects or from airborne contaminants, such as pollen, dust particles or other foreign bodies. The eyelids contain several glands including the lacrimal glands and meibomian glands that produce layers of tear film that are critical for healthy eyes. When an individual blinks, a new tear film is created and tears are distributed across the cornea to lubricate the surface of the eye. This blinking action also "flushes" foreign materials from the eye.

The eyelids, however, are subject to certain problems, which while common, are nonetheless bothersome, especially for contact lens wearers. Also, these problems may lead to other, more serious complications. One complication is staphylococcal blepharitis (blepharitis). Blepharitis is a common chronic inflammation of the eyelids characterized by a scaly crust on the lid margins. The condition may be caused by a bacterial infection, allergic in origin or associated with seborrhea of the face and scalp.

Often associated with or secondary to blepharitis is a bacterial infection of the surface of the skin at the edge of the lid, known as an internal hordeolum. Other such infections include external hordeolum, commonly referred to styes, which are infections of the tiny oil secreting meibomian glands along the edge of the eyelid, surrounding the eyelashes. A stye begins as a red, tender bump and usually fully develops within three days. It may be accompanied by pain, redness and tenderness of the lid margins. Although styes are often recurring, regular cleansing of the eyelid margins can minimize the occurrences. A second problem is a chalazion, which is an inflammation of the meibomian glands inside the eyelid. Chalazia typically grow slowly over 2-3 weeks and although they do not typically cause pain, they often require surgical intervention if left untreated.

Endophthalmitis is an intraocular infection that commonly occurs after cataract surgery. The causative agent in postoperative endopthalmitis is typically a bacteria, often the causative bacteria is *Staphylococcus Epidermidis*.

SUMMARY

Embodiments of the invention comprise a heated eyelid cleansing apparatus, a method for manufacturing a heated eyelid cleansing apparatus, a method of cleansing an eyelid with a heated eyelid cleansing apparatus and a kit for providing treatment to the eyelids.

In one embodiment of the invention, an apparatus for cleansing eyelids comprises: an eyelid cleansing composition; an absorbent pad wherein the pad is impregnated with the eyelid cleansing composition; and a heating element, wherein the heating element is encased within the absorbent pad.

In one embodiment, the eyelid cleansing composition comprises a foamable liquid. In one embodiment, the eyelid cleansing composition comprises a surfactant mixture comprising PEG-80 sorbitan laurate, sodium trideceth sulfate, PEG-150 distearate, cocamidopropyl hydroxysultaine, lauroamphocarboxyglycinate, and sodium laureth-13 carboxylate in a concentration of 7-10%; PEG-15 tallow polyamine present in a concentration of 0.1-0.5%; at least one preservative selected from the group consisting of Quaternium-15 and benzyl alcohol present in concentration of 0.1-0.5%; and disodium ethylenediaminetetraacetic acid present in a concentration of 0.0-0.1% in an aqueous solution.

In another embodiment of the invention, the eyelid cleansing composition comprises an eyelid scrub. The eyelid scrub may be effective as an anti-microbial, while being minimally irritating to the eye. The eyelid scrub comprises polyhexamethylene biguanide (PHMB), 1,2-hexanediol, 1,2-octanediol, and a pH stabilizing surfactant solution present in an amount effective to control the pH level of the composition between 5.5 and 7.5. The use of a surfactant solution to control pH rather than traditional pH adjusters, makes the composition less irritating to the eye. Also, the foaming capability of the surfactant solution included in the composition increases its cleansing ability.

In one embodiment, the pH stabilizing surfactant solution comprises cocoamphodiacetate disodium, polyoxyethylene 80 sorbitan monolaurate, decyl polyglucoside, and a modified Ringer's solution.

In another embodiment, the composition also includes moisturizers, such as methyl gluceth-20, sorbital, glycerine, glycols, propylene glycol, carboxylates, amino acids, glucoside derivatives, urea, lactates, and derivatives of pantothenic acid.

In one embodiment, the absorbent pad comprises a fabric pad. In another embodiment, the fabric pad may further comprise a first sheet of fabric and a second sheet of fabric. The first and second sheets of fabric are held together by adhesive means. In one embodiment, the first and second fabric sheets are held together by stitching or Velcro. In one embodiment, the heating element may be located within the first and second sheets of fabric.

In one embodiment, the heating element further comprises: a first packet containing a first chemical, the first chemical selected from calcium oxide, copper sulfate, water, butylene glycol, zinc, sodium silicoaluminate, kaolin, PEG 8, methyl gluceth 20, hydroxypropylcellulose, talc, acrylates copolymer, polyethelene, methycellulose, ethylcellulose, BHT, tetrasodium EDTA, or ultramarines; a second packet containing a second chemical, the second chemical selected from calcium oxide, copper sulfate, water, butylene glycol, zinc, sodium silicoaluminate, kaolin, PEG 8, methyl gluceth 20, hydroxypropylcellulose, talc, acrylates copolymer, polyethelene, methycellulose, ethylcellulose, BUT, tetrasodium EDTA, or ultramarines; and a thin membrane positioned between the first packet and the second packet.

The eyelid cleansing apparatus may further comprise means for breaking the thin membrane. In one embodiment, the means for breaking the thin membrane comprise application of a twist, snap, bend, torsion, flex or other motion.

In another embodiment, the means for breaking the thin membrane comprises an actuator. The actuator may comprise at least one sharp end, the sharp end comprising a surface sharp enough to puncture the membrane without causing significant damage to the fabric pad. In another embodiment, the actuator further comprises one or more of the following: a button, a lever, switch, or a stud.

The means for breaking the thin membrane allows the first chemical to contact the second chemical, thereby producing an exothermic reaction. The exothermic reaction heats the fabric pad to a temperature range of about 80° F. to about 150° F.

In one embodiment of the invention, the first or second sheet of fabric may further comprise a flap, wherein the first or second sheet of fabric is adapted to allow the fabric pad to be inserted and removed. The heating element may be configured to retain thermal energy when exposed to a means of heating, the means of heating including a microwave oven, conventional oven, toaster, stove, laser, flame from a lighter or a hairdryer. The heating element may further be configured to heat the fabric pad for three to seven minutes.

In another embodiment, a kit for treating eyelids comprises: an eyelid cleansing composition, the eyelid cleansing composition comprising a surfactant mixture comprising PEG-80 sorbitan laurate, sodium trideceth sulfate, PEG-150 distearate, cocamidopropyl hydroxysultaine, lauroamphocarboxyglycinate, and sodium laureth-13 carboxylate in a concentration of 7-10%; PEG-15 tallow polyamine present in a concentration of 0.1-0.5%; at least one preservative selected from the group consisting of Quaternium-15 and benzyl alcohol present in concentration of 0.1-0.5%; and disodium ethylenediaminetetraacetic acid present in a concentration of 0.0-0.1% in an aqueous solution; a fabric pad, the fabric pad pre-moistened with the eyelid cleansing composition; and a heating element. In one embodiment of the invention, the heating element is enclosed within the fabric pad.

In another embodiment, a kit for treating eyelids comprises: an eyelid cleansing composition, the eyelid cleansing composition comprising an eyelid scrub; a fabric pad pre-moistened with the eyelid scrub; and a heating element.

In one embodiment, the eyelid scrub comprises polyhexamethylene biguanide (PHMB), 1,2-hexanediol, 1,2-octanediol, and a pH stabilizing surfactant solution present in an amount effective to control the pH level of the composition between 5.5 and 7.5. In one embodiment, the pH stabilizing surfactant solution comprises cocoamphodiacetate disodium, polyoxyethylene 80 sorbitan monolaurate, decyl polyglucoside, and a modified Ringer's solution. In another embodiment, the composition also includes moisturizers, such as methyl gluceth-20, sorbital, glycerine, glycols, propylene glycol, carboxylates, amino acids, glucoside derivatives, urea, lactates, and derivatives of pantothenic acid.

In one embodiment of the invention, the heating element is enclosed within the fabric pad. In one or more embodiments, the heating element may be external to the fabric pad. The heating element may comprise a sleeve or a thermal or heating enclosure for heating the fabric pad.

In another embodiment, a method for manufacturing an heated eyelid cleansing apparatus comprises: supplying an eyelid cleansing composition; providing a fabric pad, the fabric pad capable of being moistened with the eyelid cleansing composition; and enclosing a heating element within the fabric pad. Exemplary eyelid compositions have been described earlier.

The fabric pad may be pre-moistened with the eyelid cleansing composition. In another embodiment, the fabric pad may be impregnated with the eyelid cleansing composition just prior to patient, customer use on the eyelids.

In another embodiment, a method for cleansing an eyelid comprises: heating an eyelid cleansing composition; and applying the heated eyelid cleansing composition to the eyelid. In one embodiment, the eyelid cleansing composition comprises a foamable liquid, the cleansing composition further comprising (a) an anionic surfactant, (b) a non-ionic thickener and emollient, (c) an amphoteric surfactant; and (d) at least one preservative. In another embodiment, the eyelid cleansing composition comprises an eyelid scrub comprising polyhexamethylene biguanide (PHMB), 1,2-hexanediol, 1,2-octanediol, and a pH stabilizing surfactant solution present in an amount effective to control the pH level of the composition between 5.5 and 7.5.

The heating of the eyelid cleansing composition comprises heating the eyelid cleansing composition to a range between 80° F. and 150° F. In one embodiment, the eyelid is scrubbed with the eyelid cleansing composition for a period of time ranging between 240 seconds and 500 seconds. In another embodiment, the eyelid cleansing composition may be allowed to remain on the eyelid without being rinsed away.

DETAILED DESCRIPTION

Reference is now made to one or more embodiments of the present invention, examples of which are illustrated in the accompanying drawings.

Figure 1:
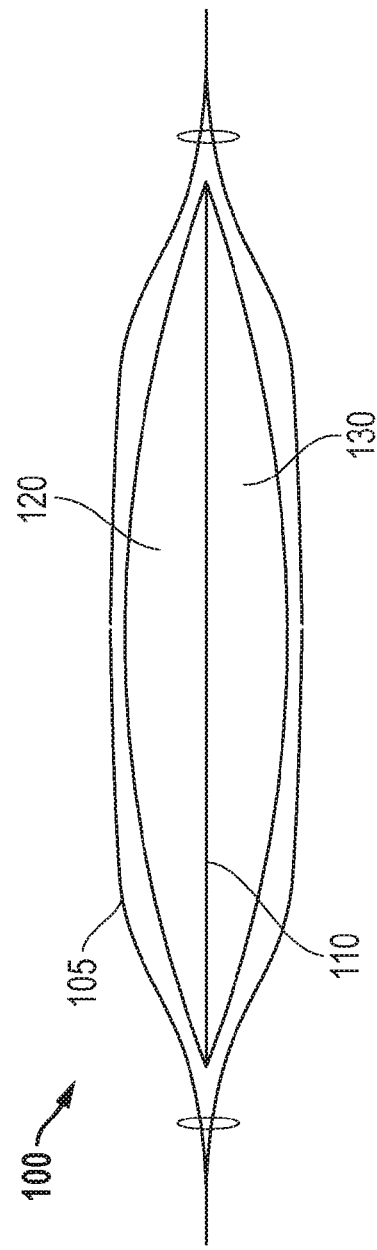
FIG. 1 is an embodiment of the invention.

FIG. 1 illustrates one embodiment of an eyelid cleansing apparatus 100. A fabric pad 105 comprises a first packet 120 and a second packet 130. The first 120 and second 130 packets contain chemical reactants that exothermically react with one another. Together, the first packet 120 and second packet 130 may form a heating element. The first packet 120 and the second packet 130 are separated within the fabric pad 105 by a thin membrane 110. The thin membrane 110, which separates a first packet 120 and a second packet 130, may be designed to be manually broken by a user. After the thin membrane 110 is broken, the chemicals from the first packet 120 are released to contact with the chemicals from the second packet 130, thereby initiating the exothermic reaction. In one embodiment, the first packet 120 may comprise a first chemical and the second packet 130 may comprise a second chemical.

The thin membrane 110 max be broken by a variety of means. In one embodiment, the means for breaking the membrane includes an actuator. An actuator may be a button, in one embodiment, which may be designed to puncture the membrane and allow the chemicals from the first packet 120 to contact and react with the chemicals from the second packet 130. The actuator may comprise a button, lever, switch, or a stud, in another embodiment. In another embodiment, the thin membrane 110 may be broken by twisting, snapping, bending, causing torsion, or flexing the membrane sufficiently so that it tears. However, it should be appreciated that the membrane may be broken by any suitable means so long as the reactants are allowed to react in an exothermic reaction.

The chemicals contained in the first packet 120 and the second packet 130 employed to create an exothermic chemical reaction may be selected from a variety of exothermic reactants including calcium oxide, copper sulfate, water, butylene glycol, zinc, sodium silicoaluminate, kaolin, PEG 8, methyl gluceth 20, hydroxypropylcellulose, talc, acrylates copolymer, polyethelene, methycellulose, ethylcellulose, BHT, tetrasodium EDTA, and ultramarines. It should be appreciated that any chemicals which react exothermically when in contact with one another may be placed in the first packet 120 and the second packet 130.

The fabric pad 105 may be impregnated with an eyelid cleansing composition. In one embodiment, the eyelid cleansing composition is optionally non-irritating to both the sensitive skin around the eye and the eye tissue itself, while having an antimicrobial effect. In one embodiment, PHMB may be used as an effective antimicrobial agent. Polyhexamethylene biguanide (PHMB) is herein pseudonymous for polyhexamethylene biguanide, polyhexamethylene biguanide hydrochloride, and polyaminopropyl biguanide. In another embodiment, a combination of 1,2-hexanediol and 1,2-octanediol with PHMB may be used because it has a synergistic antimicrobial effect.

PHMB may be optimally effective at pH ranges between 5.5 and 7.5. Therefore, it may be desirable to control the pH level of the eyelid cleansing composition within this range by use of a blend of surfactants. It may also be desirable that the eyelid cleansing composition of the invention has a foaming ability to facilitate physical cleansing of the eyelid. Consequently, surfactants may be chosen which will both control the pH of the eyelid cleansing composition within PHMB's effective range and provide the foaming ability to physically clean the eyelid.

In another embodiment, the pH of the eyelid cleansing solution may be controlled in order to minimize eye irritation caused by an abnormal pH level of the eyelid cleansing composition. Non-irritating formulations may have a pH level which is close to neutral, or 7.0. Many skin cleaners have a pH that is not neutral and thus not at or near the 7.0 pH level. In order to neutralize the pH of the compositions, a pH adjuster may be used to adjust the pH level. Examples of traditional pH adjusters include basic pH adjusters, such as ammonia, mono-alkyl amines, di-alkyl amines, tri-alkyl amines, mono-alkanolamines, di-alkanolamines tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine), and acidic pH adjusters, such as mineral acids and polycarboxylic acids (e.g., hydrochloric acid, nitric acid, phosphoric acid, sulfuric acid, citric acid, glycolic acid, and lactic acid). However, some adjusters may cause irritation themselves.

In one embodiment, the pH of the eyelid cleansing composition is controlled with a surfactant solution rather than traditional pH adjusters. A surfactant may be less irritating to the eye than traditional pH adjusters. Suitable surfactants to be used in the pH stabilizing surfactant solution include amphoteric surfactants, anionic surfactants, and nonionic surfactants. Suitable amphoteric surfactants include, but are not limited to alkyldimethyl betaines, alkylamido betaines, sulfobetaines, and imidazoline amphoterics. Suitable anionic surfactants include, but are not limited to, fatty alcohol sulfates, alpha olefin sulfonates, sulfosuccinates, sarcosinates, phosphate esters, and carboxylates. Suitable nonionic surfactants include, but are not limited to, alkanolamids, ethoxylate amids, esters, alxylated alcohols, alkylpolyglucosides, amine oxides, sorbitan esters, and ethoxylates.

In one embodiment, the pH stabilizing surfactant solution comprises cocoamphodiacetate disodium, polyoxyethylene 80 sorbitan monolaurate, decyl polyglucoside, and a modified Ringer's solution. Cocoamphodiacetate disodium is an amphoteric surfactant. Polyoxyethylene 80 sorbitan monolaurate and decyl polyglucoside are both nonionic surfactants. In another embodiment, the eyelid cleansing composition, when mixed, comprises about 0.1 to 25 wt. % cocoamphodiacetate disodium, 0.1 to 10 wt. % polyoxyethylene 80 sorbitan monolaurate, 0.2 to 10 wt. % decyl polyglucoside, and 60 to 98 wt. % modified Ringer's solution.

In addition to reduced irritation, main surfactants have the added capability of producing foam which assists in the cleansing ability of the eyelid cleansing composition. To form the pH stabilizing surfactant solution, one or more foam producing surfactants are first selected to provide the foaming ability of the eyelid cleansing composition. Suitable surfactants include anionic, nonionic, and amphoteric surfactants. In one embodiment, both polyoxyethylene 80 sorbitan monolaurate and decyl polyglucoside are used as the foam producing surfactants.

In this embodiment, one or more additional surfactants may be added to the pH stabilizing surfactant solution to compensate for the pH level of the foam producing surfactants. In one embodiment, the pH of the foam producing surfactants may be measured to determine whether a pH compensating surfactant should be added, and if so, a pH compensating surfactant may be chosen to control the pH of the solution within the desired range. For example, if the pH level of the foam producing surfactants is in the acidic range, i.e. less that 7.0, a pH compensating surfactant in the basic range may be chosen. Suitable pH compensating surfactants include both foaming and non-foaming surfactants, which further include anionic, nonionic, and amphoteric surfactants. In one embodiment, the pH compensating surfactant may be cocoamphodicetate disodium.

The combination of surfactants may be added to a modified Ringer's solution. A modified Ringer's solution may be an isotonic aqueous solution of electrolytes which may be physiologically compatible with human tissue and may comprise sodium chloride, potassium chloride, calcium chloride, and water. In another embodiment, the modified Ringer's solution may be included in the surfactant solution to ensure that the eyelid cleansing composition will not remove water from human tissue by osmosis.

The modified Ringer's solution comprises sodium chloride, potassium chloride, calcium chloride, and water. In a further embodiment, the water used is purified water. The modified Ringer's solution may also comprise 0.05 to 1.2 wt. % sodium chloride, 0.005 to 0.5 wt. % potassium chloride, 0.005 to 0.5 wt. % calcium chloride, and water. In still another embodiment, the modified Ringer's solution comprises about 0.7 wt. % sodium chloride, about 0.03 wt. % potassium chloride, about 0.033 wt. % calcium chloride, and purified water.

In still another embodiment, the eyelid cleansing composition may further comprise one or more moisturizers. Moisturizers are chemicals that prevent transepidermal water loss. Moisturizers may prevent water loss by forming a film over the skin to prevent water from evaporating from the skin. Alternatively, moisturizers comprise hydroscopic molecules that draw water from the air into the skin. Suitable moisturizers include, but are not limited to, methyl gluceth-20, sorbital, glycerine, propylene glycol, carboxylates, amino acids, glucoside derivatives, urea, lactates, and derivatives of pantothenic acid. Examples of derivatives of pantothenic acid include panthenol, D-panthenol, and D,L-panthenol.

In a further embodiment, the eyelid cleansing composition also comprises a foam stabilizer. A foam stabilizer is a chemical which increases the lifetime of the foam. The foam stabilizer can be a polyethylene glycol diester of methyl glucose and a fatty acid. Suitable fatty acids include oleic acid, steric acid, lauric acid, caprylic acid, and capric acid. Suitably, the foam stabilizer may be PEG-120 methyl glucose dioleate.

In another embodiment, the eyelid cleansing composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate.

In another embodiment of the invention, the eyelid cleansing composition comprises about 0.02 wt. % to about 0.3 wt. % PHMB, about 0.05 wt. % to about 2.0 wt. % 1,2-hexanediol, about 0.05 wt. % to about 2.0 wt. % 1,2-octanediol, about 0.1 wt. % to about 25 wt. % cocoamphodiacetate disodium, about 0.1 wt. % to about 10 wt. % polyoxyethylene 80 sorbitan monolaurate, about 0.2 wt. % to about 10 wt. % decyl polyglucoside, and about 60 wt. % to about 98 wt. % modified Ringer's Solution.

In yet another embodiment of the invention, the eyelid cleansing composition comprises about 0.04 wt. % polyhexamethylene biguanide, about 0.2 wt. % 1,2-hexanediol, about 0.2 wt. % 1,2-octanediol, about 0.2 wt. % D-panthenol, about 0.215 wt. % cocoamphodiacetate disodium, about 4.032 wt. % polyoxyethylene 80 sorbitan monolaurate, about 0.275 wt. % decyl polyglucoside, about 4.3 wt. % methyl gluceth-20, about 0.6 wt. % PEG-120 methyl glucose dioleate, about 87.985 wt. % Modified Ringer's solution, and water.

In another embodiment, the combination of surfactants comprises an aqueous solution of approximately 7% to approximately 10% by weight combination of an anionic surfactant, a non-ionic thickener, an emollient and an amphoteric surfactant.

In yet another embodiment, the combination of surfactants may comprise PEG-80 sorbitan laurate, sodium trideceth sulphate, PEG-150 distearate, cocamidopropylhydroxy sultaine, lauroamphocarboxy glycinate, and sodium laureth-13 carboxylate. In still another embodiment, the eyelid cleansing composition may comprises a polyoxyetln lenesorbitan fatty acid ester, PEG-80 sorbitan laurate, lauroamphocarboxy glycinate and sodium laureth-13 carboxylate.

The eyelid cleansing composition may further comprise PEG-15 tallow polyamine in a concentration range of 0.1-0.5% by weight. This compound is a tertiary surfactant and emollient. Sodium chloride may also be present in a concentration ranging from about 0.6% to about 0.9%. In this embodiment, the pH of the eyelid cleansing composition may be in the range of about 8.0 to about 8.5.

A preservative may also be included in the eyelid cleansing composition. In one embodiment, the preservative may be quaternium-15, a quaternary ammonium salt. This preservative may be used in a concentration range of approximately 0.1% to approximately 0.5%. In another embodiment, benzyl alcohol may be used as a preservative. In this embodiment, the concentration range of the benzyl alcohol may be about 0.1% to about 0.5%.

In still another embodiment, a chelating agent such as disodium EDTA may be included in the eyelid cleansing composition in a concentration range of about 0.01% to about 0.1%.

Zinc salts are astringents which cause skin to tighten. The skin around the ocular area may be more sensitive that other areas of skin. The inclusion of a zinc salt in the eyelid cleansing composition may be undesirable as its astringent property would make the eyelid cleansing composition more irritating to the eyelid area. Therefore in one embodiment, the eyelid cleansing composition comprises PHMB, 1,2-hexanediol, 1,2-octanediol, and a pH stabilizing surfactant solution, but is also essentially free of zinc salts. Examples of zinc salts include zinc acetate, zinc lactate, zinc gluconate, zinc citrate, zinc butyrate, and zinc sterate.

Referring to FIG. 1, a fabric pad 105 may be used for the delivery of the eyelid cleansing composition. The fabric pad 105 may be composed of any suitable fabric. In one embodiment, suitable fabric is capable of containing the eyelid cleansing composition in the interstitial spaces of fabric's weave. The fabric chosen may have a textured surface which is sufficient to provide for proper scrubbing action of the eyelid cleansing composition over the patient's eyelid. However, it max remain soft enough so as to not be harsh on the patients' skin surface. In one embodiment, the fabric pad may be composed of a rayon material and polypropylene fabric blend.

Figure 2:
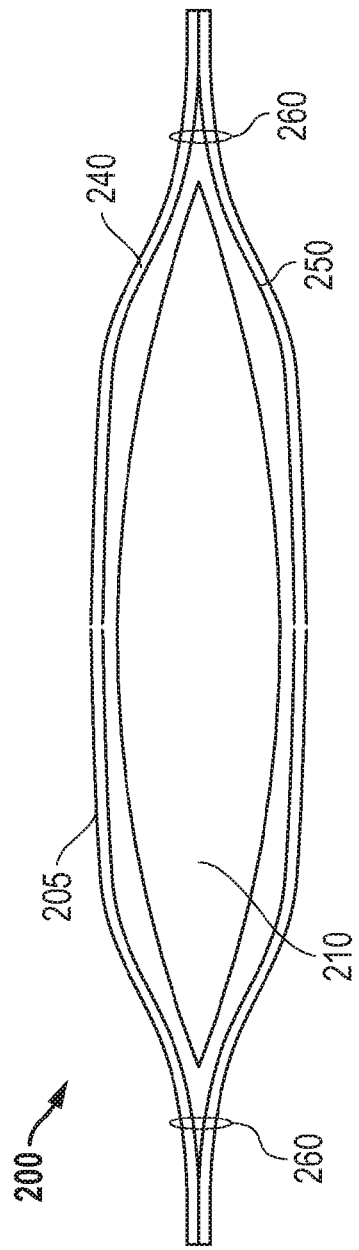
FIG. 2 is another embodiment of the invention.

As shown in FIG. 2, in another embodiment of the eyelid cleansing apparatus 200, the fabric pad 205 may comprise two sheets of fabric, a first sheet of fabric 240 and a second sheet of fabric 250. The two sheets of fabric max be held together by stitching 260 on the sides. A heating element 210 max be enclosed within the first 240 and second 250 sheets of fabric.

In one embodiment, the fabric pad 105, 205 with the enclosed heating element may be impregnated with the eyelid cleansing composition at the time of manufacture. The fabric pad 105, 205 may then be sealed within a container to prevent the eyelid cleansing composition from evaporating. The sealable container max comprise a box or a package. The package may be made of any suitable material including plastic or a metal foil material. The pre-moistened fabric pads 105, 205 may also be individually packaged for use.

In another embodiment, the fabric pad 105, 205 with the enclosed heating element may be impregnated with the eyelid cleansing composition moments prior to use. The eyelid cleansing composition may be packaged separately from the fabric pad 105, 205 and applied to the fabric pad 105, 205 by the user. In one embodiment, the eyelid cleansing composition may be packaged in a foaming pump dispenser.

In one embodiment of the invention, the eyelid cleansing apparatus 100, 200 may be heated prior to application to the ocular area. When heated, the eyelid cleansing composition on the fabric pad is also heated which may serve to increase the efficiency of the eyelid cleansing composition.

The heat transferred to the eyelid cleansing apparatus 100, 200 and eyelid cleansing composition may be sufficient enough to bring the temperature of the eyelid cleansing composition to a temperature which aids in cleansing of the ocular area while maintaining a temperature low enough not to scald the patient's skin or otherwise cause discomfort. In one embodiment, the eyelid cleansing apparatus 100, 200 may be heated to maintain the temperature of the eyelid cleansing composition in a range of about 80° F. to about 150° F.

In another embodiment, the eyelid cleansing apparatus 100, 200 may sustain heat long enough to complete the cleansing process. The exact time required for cleansing the eyelid may vary from patient to patient and may further depend on the severity of the patient's condition. In one embodiment, the eyelid cleansing apparatus 100, 200 may maintain heat for approximately 3 minutes to 7 minutes.

Referring to FIG. 2, in another embodiment of the eyelid cleansing apparatus 200, a heating element 210 after being externally heated may be placed within the fabric pad 205. In this embodiment, the fabric pad 205 may comprise a flap (not shown) for inserting the heating element 210. The flap is closed after the heating element 210 is enclosed. It should be appreciated that the heating element 210 may be encased in the fabric pad 205 by any suitable means known in the art including stitches 260 or Velcro.

The heating element 210 may be heated by any reasonable means including heating in a microwave oven, conventional oven, toaster, stove, laser, flame from a lighter, or a hair dryer. However, it should be appreciated that the means of heating are not limited to those listed and could be any potential means which produce heat.

Figure 3:
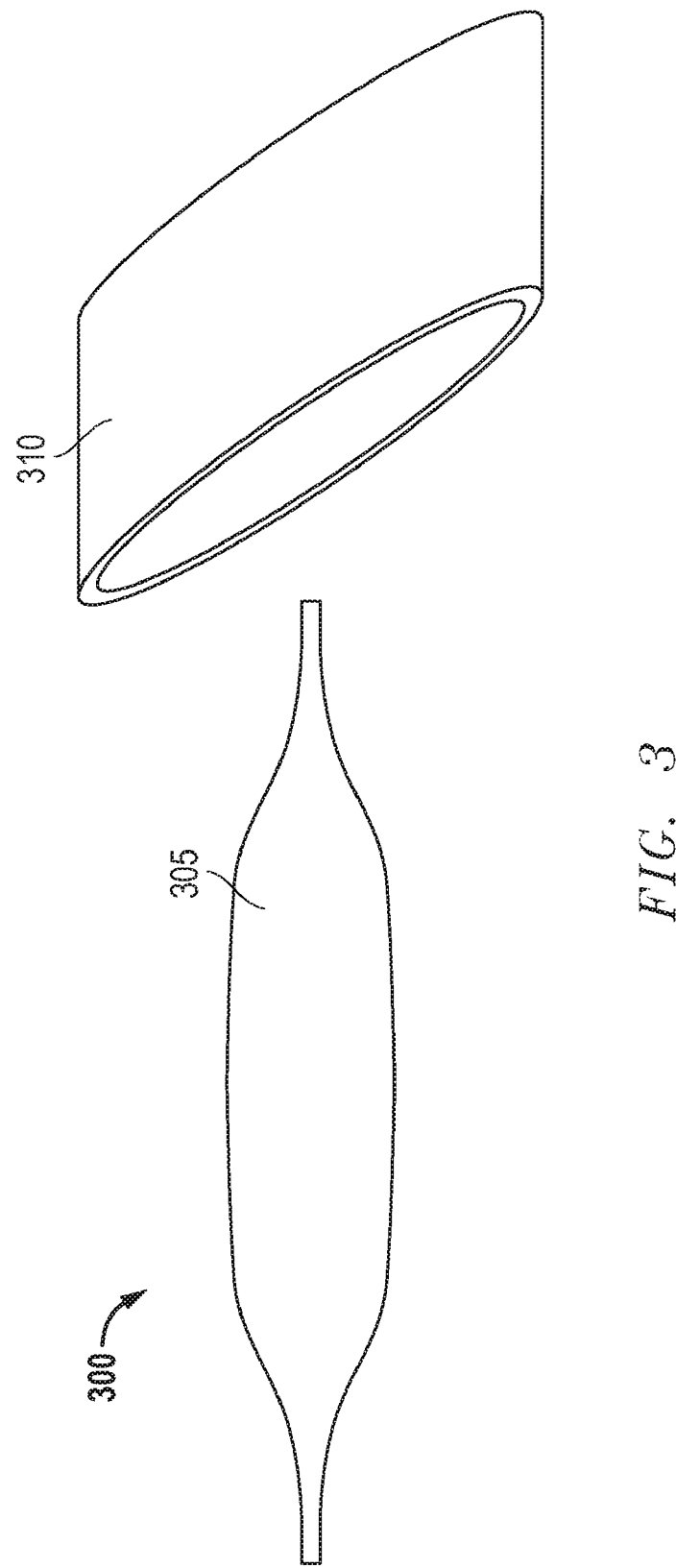
FIG. 3 is yet another embodiment of the invention.

FIG. 3 represents another embodiment of the eyelid cleansing apparatus 300, wherein the fabric pad 305 is heated by being placed in a heating or thermal sleeve 310 for a certain time period. The thermal sleeve 310 may be heated by means of a heating device. In one embodiment, the thermal sleeve 310 may first be warmed, for example, in a microwave oven. The thermal sleeve 310 may be heated until it retains enough thermal energy for heating the fabric pad 305. Once the thermal sleeve 310 is heated, the fabric pad 305 may be placed inside of it so that heat may be transferred from the thermal sleeve 310 to the fabric pad 305, thereby warming the fabric pad 305. In one embodiment, the fabric pad is impregnated with the one or more exemplary eyelid cleansing compositions described earlier. The heated fabric pad 305 may then be easily removed from the heating sleeve 310. A user may apply the heated fabric pad 305 to the ocular area. The fabric pad 305 may be pre-moistened with the eyelid cleansing composition or the eyelid cleansing composition may be placed on the fabric pad 305 by the user at the time of use.

In one embodiment of the invention, the eyelid cleansing apparatus 100, 200, 300 is used to cleanse the eyelids. The eyelid cleansing apparatus 100, 200, 300 may be useful in preoperative sterilization of the eyelid and in everyday application for the prevention of various diseases of the eyelid, such as blepharitis.

The eyelid cleansing composition may be mild enough that it can be allowed to remain on the eyelid after cleansing, without rinsing. Allowing the eyelid cleansing composition to be left on the eyelid rather than rinsing it off may increase the eyelid cleansing composition's anti-microbial effect. In general, the longer an anti-microbial eyelid cleansing composition is allowed to contact the pathogens, the more pathogens it may kill.

While the invention has been described with reference to several embodiments, it will be understood by those skilled in the art that various changes in form and detail may be made therein without departing from the spirit and scope of the invention. Thus, it is intended that the present invention cover the modifications and variations of this invention provided that they come within the scope of any claims and their equivalents.

The invention claimed is:

1. An apparatus for cleansing eyelids, comprising:
    an eyelid cleansing composition: an absorbent pad, the pad impregnated with the eyelid cleansing composition, an heating clement, wherein the heating element is encased within the absorbent pad, and wherein the eyelid cleansing composition comprises: polyhexamethylene biguanide; 1,2-hexanediol, 1,2-octanediol, and a pH stabilizing surfactant solution present in an amount effective to control the pH level of the composition between 5.5 and 7.5.

2. The apparatus of claim 1, wherein the eyelid cleansing composition is a foamable liquid, scrub, gel, ointment, cream, lotion or paste.

3. The apparatus of claim 1, wherein the eyelid cleansing composition further comprises: a surfactant mixture comprising PEG-80 sorbitan laurate, sodium trideceth sulfate, PEG-150 distearate, cocamidopropyl hydroxysultaine, lauroamphocarboxyglycinate, and sodium laureth-13 carboxylate in a concentration of 7-10%: PEG-15 tallow polyamine present in a concentration of 0.1-0.5%:
    at least one preservative selected from the group consisting of Quaternium-15 and benzyl alcohol present in concentration of 0.1-0.5%: and disodium ethylenediaminetetraacetic acid present in a concentration of 0.0-0.1% in an aqueous solution.

4. The apparatus of claim 1, wherein the pH stabilizing surfactant solution is comprised of one or more surfactants selected from a group consisting of amphoteric surfactants, anionic surfactants, and nonionic surfactants.

5. The apparatus of claim 4, wherein the amphoteric surfactants are selected from a group consisting of: alkyldimethyl betaines, alkylamido betaines, sulfobetaines, and imidazoline amphoterics.

6. The apparatus of claim 4, wherein the anionic surfactants are selected from a group consisting of: fatty alcohol sulfates, alpha olein sulfonates, sulfosuccinates, sarcosinates, phosphate esters, and carboxylates.

7. The apparatus of claim 4, wherein the nonionic surfactants are selected from a group consisting of: alkanolamids, ethoxylate amids, esters, alkylated alcohols, alkylpolyglucosides, amine oxides, sorbitan esters and ethoxylates.

8. The apparatus of claim 1, wherein the pH stabilizing surfactant solution comprises: cocoamphodiacetate disodium: polyoxyethylene 80 sorbitan monolaurate: decyl polyglucoside: and a modified Ringer's solution.

9. The apparatus of claim 8, wherein the modified Ringer's solution comprises: sodium chloride; potassium chloride; calcium chloride; and water.

10. The apparatus of claim 1, wherein the eyelid cleansing composition further comprises: D-panthenol; methyl gluceth 20; and PEG-120 methyl glucose dioleate.

11. The apparatus of claim 1, wherein the eyelid cleansing composition further comprises one or more moisturizers.

12. The apparatus of claim 1, wherein the absorbent pad comprises a fabric pad.

13. The apparatus of claim 12, wherein the fabric pad further comprises a first sheet of fabric and a second sheet of fabric, the heating element positioned within the first and second sheets of fabric.

14. The apparatus of claim 13, wherein the fabric pad further comprises adhesive means for holding together the first and second sheets of fabric.

15. The apparatus of claim 1, wherein the heating element further comprises:
    a first packet containing a first chemical, the first chemical selected from calcium oxide, copper sullfate, water, butylene glycol, zinc, sodium silicoaluminate, kaolin, PEG 8, methyl gluceth 20, hydroxypropylcellulose, talc, acrylates copolymer, polyethylene, methylcellulose, ethylcellulose, BHT, tetrasodium EDTA, or ultramarines:
    a second packet containing a second chemical, the second chemical selected from calcium oxide, copper sulfate, water, butylene glycol, zinc, sodium silicoaluminate, kaolin, PEG 8, methyl gluceth 20, hydroxypropylcellulose, talc, acrylates copolymer, polyethylene, methycellulose, ethylcellulose, BHT, tetrasodium EDTA, or ultramarines; and a thin membrane positioned between the first packet and the second packet.

16. The apparatus of claim 15, further comprising a means for rupturing the thin membrane.

17. The apparatus of claim 16, wherein the rupturing means comprise application of a twist, snap, bend, torsion, flex or other motion.

18. The apparatus of claim 16, wherein the rupturing means comprises an actuator.

19. The apparatus of claim 18, wherein the actuator comprises at least one sharp end, the sharp end comprising a surface sharp enough to puncture the membrane without causing significant damage to the fabric pad.

20. The apparatus of claim 18, wherein the actuator further comprises one or more of the following: a button, a lever, switch, or a stud.

21. The apparatus of claim 16, wherein rupturing the thin membrane allows the first chemical to contact the second chemical, thereby producing an exothermic reaction.

22. The apparatus of claim 21, wherein the exothermic reaction heats the fabric pad to a temperature range of about 80° F. to about 150° F.

23. A kit for treating eyelids comprising: an eyelid cleansing composition:
a fabric pad, the fabric pad pre-moistened with the eyelid cleansing composition:
and means for providing thermal energy to the fabric pad.

24. The kit of claim 23, wherein the eyelid cleansing composition comprises: a surfactant mixture comprising PEG-80 sorbitan laurate, sodium trideceth sulfate, PEG-150 distearate, cocamidopropyl hydroxysultaine, lauroamphocarboxyglycinate, and sodium laureth-13 carboxylate present in a concentration of 7-10%: PEG-15 tallow polyamine present in a concentration of 0.1-0.5%: at least one preservative selected from the group consisting of Quaternium-15 and benzyl alcohol present in concentration of 0.1-0.5%: and disodium ethylenediaminetetraacetic acid present in a concentration of 0.0-0.1%, in an aqueous solution.

25. The kit of claim 23, wherein the eyelid cleansing composition further comprises: polyhexamethylene biguanide: 1,2-hexanediol: 1,2-octanediol: and a pH stabilizing surfactant solution present in an amount effective to control the pH level of the composition between 5.5 and 7.5.

26. The kit of claim 23, wherein the means for providing thermal energy further comprise a heating sleeve.

27. The kit of claim 23, wherein the means for providing thermal energy further comprise a heating element positioned within the fabric pad.

* * * * *